(12) United States Patent
Reif et al.

(10) Patent No.: US 6,959,812 B2
(45) Date of Patent: Nov. 1, 2005

(54) FILTER PACKAGE

(75) Inventors: Oscar-Werner Reif, Hannover (DE); Andreas Graus, Nörten-Hardenburg (DE)

(73) Assignee: Sartorius AG, Goettingen (DE)

( * ) Notice: Subject to any disclaimer, the term of this patent is extended or adjusted under 35 U.S.C. 154(b) by 643 days.

(21) Appl. No.: 10/214,896

(22) Filed: Aug. 7, 2002

(65) Prior Publication Data

US 2003/0029763 A1 Feb. 13, 2003

(30) Foreign Application Priority Data

Aug. 9, 2001 (DE) ................. 101 39 291

(51) Int. Cl.[7] .............................................. B65D 75/64
(52) U.S. Cl. ....................... 206/469; 206/438
(58) Field of Search ................ 206/363–370, 206/438, 469, 525, 531, 532, 534, 570–572; 604/192–198, 604/263

(56) References Cited

U.S. PATENT DOCUMENTS

| | | | | |
|---|---|---|---|---|
| 3,036,700 A | * | 5/1962 | Krug ........................ | 206/365 |
| 3,074,540 A | * | 1/1963 | Beich et al. ............... | 206/366 |
| 3,255,880 A | * | 6/1966 | Grossman .................. | 206/469 |
| 4,444,310 A | * | 4/1984 | Odell ........................ | 206/366 |
| 5,038,929 A | * | 8/1991 | Kubofcik ................... | 206/365 |
| 5,219,529 A | * | 6/1993 | Ngo et al. ................. | 206/534 |
| 5,347,078 A | * | 9/1994 | Eckels ...................... | 206/365 |
| 5,707,173 A | * | 1/1998 | Cottone et al. ............ | 206/366 |
| 5,971,966 A | * | 10/1999 | Lav .......................... | 604/263 |
| 6,010,444 A | * | 1/2000 | Honeycutt et al. ......... | 206/366 |
| 6,398,031 B1 | * | 6/2002 | Frezza ...................... | 206/571 |
| 6,773,427 B2 | * | 8/2004 | Takagi ...................... | 206/828 |
| 2005/0103666 A1 | * | 5/2005 | Grimard et al. ........... | 206/438 |

* cited by examiner

Primary Examiner—Jim Foster
(74) Attorney, Agent, or Firm—Chernoff, Vilhauer, McClung & Stenzel, LLP

(57) ABSTRACT

There is disclosed a filter package comprising a housing and a cover that is adapted to enclose a sterile disposable filter wherein the package cover is penetrable at a point axially aligned with the filter and has at least one pre-formed break line along which the package cover, when subjected to appropriate force, ruptures so as to permit withdrawal of the filter by a syringe coupled thereto.

13 Claims, 2 Drawing Sheets

FILTER PACKAGE

Persuant to 35 USC 119, the priority of DE 101 39 291.5 filed Aug. 9, 2001 is claimed.

BACKGROUND OF THE INVENTION

Sterile disposable filters are employed in medicine to guard against contamination, particularly as an insert in syringes, intravenous cannulas, probes or infusion means. In the pharmaceutical and microbiology industries such disposable filters have applications in laboratories for the intake or through-flow of liquids, which must be freed of contamination; in such applications the disposable filter is inserted between a syringe body and its associated penetrating needle or cannula.

Such disposable filters are commercially available as Minisart® filters from Sartorius AG of Göttingen, Germany. Such filters generally comprise a sterile filter membrane encapsulated in a filter holder. The filter holder typically is provided with a connection for the syringe body and for the syringe needle, both in the form of female/male Luer Lock® connectors. An infusion line or a syringe needle can be coupled to the needle connection. The disposable filter can be used as a pre-filter for an optional liquid container, which itself can be equipped with a Luer Lock® connector. The syringe body generally has a conically shaped connection piece on its discharge end which is capable of being coupled to the syringe connection of the filter holder. The filter membrane is to prevent contaminating materials, which may be present in the syringe liquid, from migrating into the so-called downstream zone, that is, into the area of the needle or fluid discharge line.

The disposable filter is in a filter package comprising a package housing and a package cover and disposed therein in such a manner that the syringe connection of the disposable filter is proximal to the package cover. The package cover is sealed airtight with the housing by adhesive. The filter and the entire filter package are sterilized.

Existing filter packages have an integral square package cover provided with a tab on each corner for tearing off the cover in order to expose the syringe connection. Manipulation of this known filter package to remove its cover is somewhat cumbersome and time-consuming. In order to open the filter package, the package housing must be firmly grasped with one hand, while the other hand seizes a tab and tears off the cover. To do this, the syringe must first be laid down, sometimes compromising sterility. In surgical and emergency activities, a quick and simple manipulation that maintains sterility is very important.

Punch-through bottles are known, which have a cover which can be penetrated by a cannula, in order to withdraw a fluid by means of a syringe. Such a cover, however, is not well-adapted to make the above manipulation easier, since this cover, in the same manner as the cover of the known filter package, must be removed before the withdrawal of a generally flat-shaped filter.

It is therefore an object of the present invention to an improved filter package that may be manipulated more simply and more rapidly and that does not compromise sterility.

BRIEF SUMMARY OF THE INVENTION

The foregoing object is achieved by the provision of a package cover that can be penetrated at a penetration point which is in axial alignment with the syringe. The cover is also provided with pre-formed break lines, along which the package cover, upon an appropriate exertion of force, ruptures in such a manner that the disposable filter becomes removable by the folding out of the package segments which are formed by the break lines. Because the package cover has pre-formed break lines, a removal of the disposable filter from the filter package is possible without the need to lay down either the syringe or the package.

The pre-formed break lines are so designed, that a contamination-tight closure of the filter package is assured. Using the syringe's cone portion, the package cover can be easily penetrated at its penetration point and the syringe cone sealingly received by the syringe connection of the filter. In the course of a subsequent pulling motion coupled with the simultaneous gripping of the package housing, a pressure on the filter holder is exerted from the inside of the package cover, causing the cover to tear along the break lines into flap-shaped segments. As this is in progress, the flaps of the package cover segments fold out upwards and the disposable filter can be easily withdrawn. Thus, the coupling of the syringe and the filter and the withdrawal of the filter from its packaging may be accomplished in a single step.

DETAILED DESCRIPTION OF PREFERRED EMBODIMENTS

Figure 1:
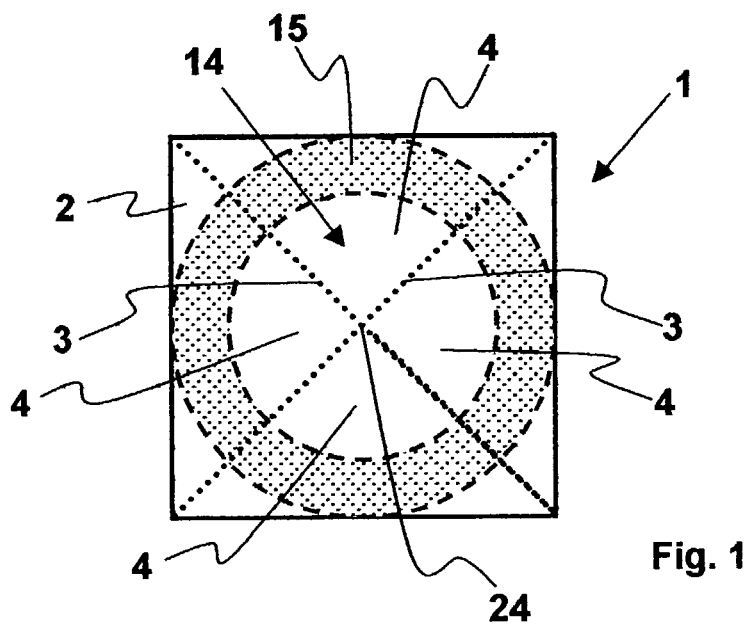
FIG. 1 is a plan view of an exemplary filter package of the invention featuring the package cover.
Figure 3:
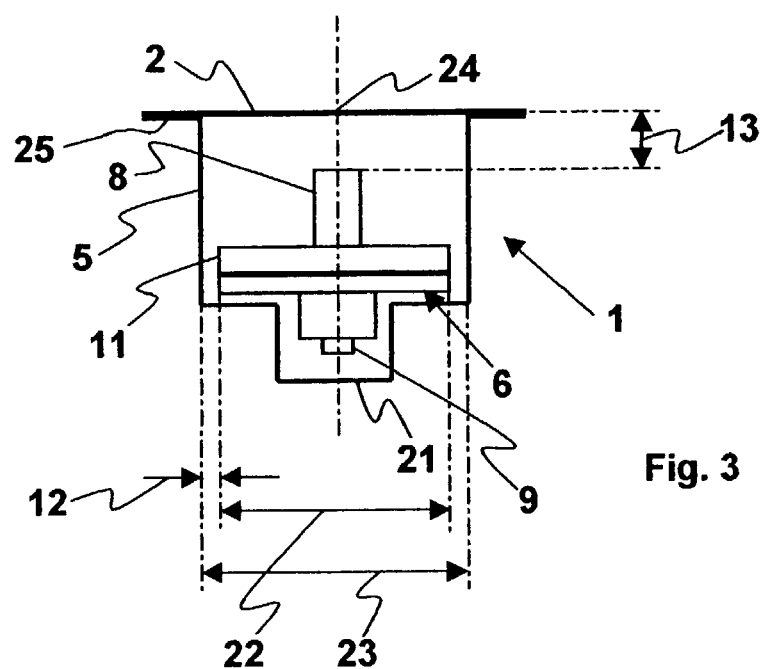
FIG. 3 is a sectional side view of the filter package of the invention with a disposable filter disposed therein.
Figure 4:
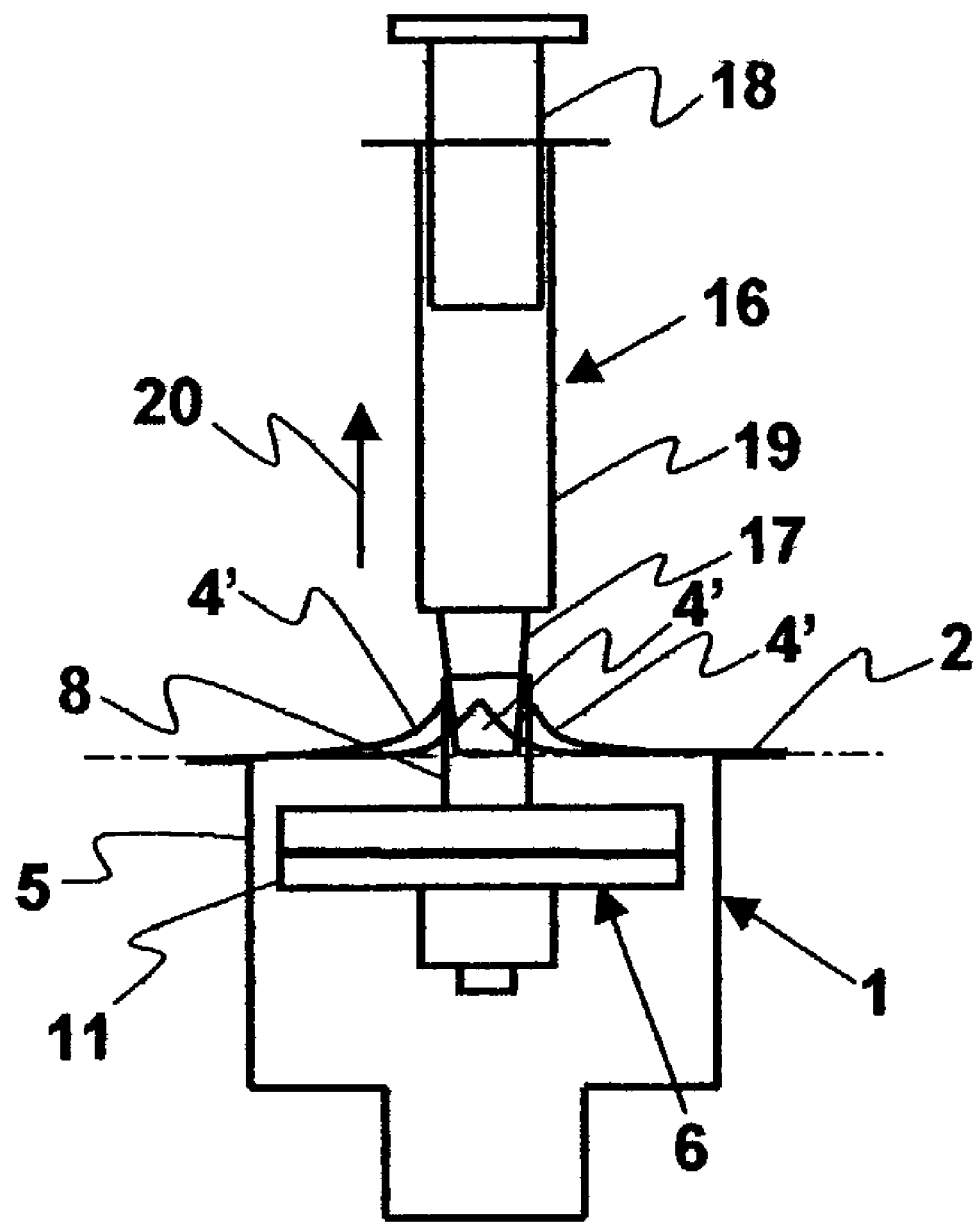
FIG. 4 is another sectional side view of FIG. 3 showing a schematic of a syringe coupled to a disposable filter with the syringe/filter combination ready for withdrawal from the package.

Referring to the drawings, wherein like numerals refer to the same elements, there is shown in FIGS. 1 and 3–4 an exemplary filter package 1 for enclosing a sterile disposable filter 6, comprising housing 5 and square cover 2.

As seen in FIG. 1 the cover 2 is provided with two pre-formed partially perforated or scored or stamped break lines 3 crossing each other that originate from the corners of cover 2, the intersection of which forms penetration point 24 and divides cover 2 into four segments 4.

Housing 5 preferably is provided with a square flange 25 that surrounds the periphery of a circular housing opening 14 having a diameter 23. A circular adhesion surface 15 is located on flange 25, by means of which cover 2 is sealed airtight to housing 5. The corners of cover 2 can be designed as tabs (not shown), which, if necessary, could serve to open the package by pulling off cover 2.

Figure 2:
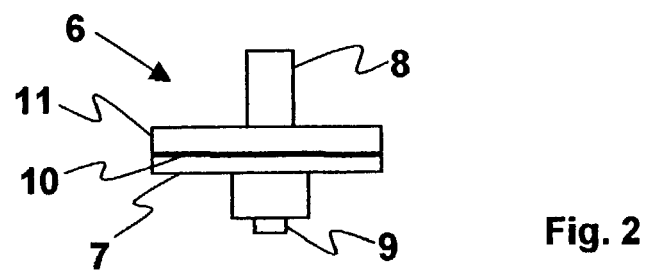
FIG. 2 is a side view of a disposable filter.

A disposable filter 6 shown in FIG. 2 consists of a circular filter holder 7 having a diameter 22, which encloses a sterile filter membrane 10. Filter holder 7 is preferably provided with a syringe connection 8, preferably in the form of a female Luer Lock® connector.

A syringe 16 may be coupled with syringe connection 8 via a male Luer Lock® connector. The other side of filter membrane 10 is provided with a needle connection 9, preferably in the form of a male Luer Lock® connector. Needle connection 9 consists of an inner, continuous hollow cylinder which is in fluid communication with filter membrane 10, which is adapted to receive a conically shaped connection piece of a needle (not shown) and an outer cylindrical flange (not shown), which lends to the connected needle a lateral stability.

Syringe 16 consists of piston 18 and body 19, the lower end of which forms a discharge cone 17, best seen in FIG. 4. Female syringe connection 8 can be snugly secured to cone 17, which is preferably provided with a male Luer Lock® connector. The provision of Luer Lock® connectors allows the coupling of intermediate elements that are in fluid communication with the syringe/filter holder assembly, and that are similarly provided with Luer Lock® connectors. Luer Lock® connectors provide a fail-safe means for prevention of a possible breach of the connection between the filter 6 and the particular application. Generally, it is sufficient in the case of coupling with a syringe to simply plug syringe cone 17 into syringe connection 8 as in FIG. 4, and similarly to push a cannula into needle connection 9 to obtain a stable and tight connection.

Liquid can be forced through filter 6 by activating syringe piston 18, which permits filter membrane 10 to filter out any contamination, so that the liquid delivered from syringe 16 is absolutely sterile. In such a flow direction the side of filter membrane 10 proximal to filter holder 7 is the downstream side.

A reverse liquid flow is also possible, wherein a liquid is drawn through filter 6, which is now in an upstream position relative to the flow, into syringe 16 with the downstream zone on the side of syringe connection 8. However, this side is not particularly protected from contamination, since syringe cone 17, upon penetration of cover 2, comes into contact with the non-sterile outside of the cover. Such a reverse withdrawal mode is thus only adaptable for such applications wherein sterility is not essential. Accordingly, references herein to the downstream zone refer only to that side of filter membrane 10 proximal to needle connection 9.

FIG. 3 depicts disposable filter 6 disposed within filter package 1. Between syringe connection 8 and cover 2, a clearance 13 is provided so that, upon penetration of cover 2 at penetration point 24 by syringe cone 17, the resulting four flaps of the penetrated cover, which are consequently pushed out of the way downwardly, do not touch syringe connection 8. In this way, when the connection is made between syringe 16 and filter 6, no residual remnants of package cover 4 intervene between cone 17 and the inner wall of syringe connection 8.

In FIG. 3, there is shown another space 12 provided between a circumferential outer flange 11 of filter holder 7 and an inner wall of housing 5. In order to provide additional protection of the downstream zone from contamination, outer flange 11 can be snugly fit against the walls of housing 5. In other words, the diameters 22 and 23 of filter 6 and housing 5 are made to be substantially equal, so that space 12 substantially disappears.

To remove filter 6 from its package, package cover 2 is first penetrated by the syringe cone 17 at penetration point 24. Next, cone 17 is firmly seated in syringe connection 8. Then filter 6 is moved in the withdrawal direction 20, now trailing behind syringe 16. With this movement, the syringe connection 8 presses against cover 2. Thereupon, cover 2 begins to break open along break lines 3, so that package cover segments 4' flap open to the outside of the package in the direction 20. By continued pulling in the direction 20, a tensional force is exerted by the entire surface of filter holder 7 from the inside against cover 2, so that the segments 4' fold completely upward and filter 6 is entirely removed from its package. Removal of filter 6 can also be accomplished by pushing against pliable segment 21 of the package housing while firmly holding housing 5 somewhere in the area of flange 25, which causes filter holder 7 to bear upwardly against cover 2, which in turn overcomes the tear resistance of break lines 3.

In a preferred embodiment of the invention, the package cover is provided with two break lines by scoring, stamping, embossing or by partial perforation, the break lines intersecting one another, and the point of intersection forming a penetrable point. In this way, the package cover may be divided into four segments. This mode of construction is of especial advantage for conventional filter packages with a circular housing wherein circular disposable filters are relatively tightly fitted, and which have round or square covers. The crossing break lines divide the cover into four equally sized segments and the intersection of the break lines forming the penetration point is necessarily axially aligned to the syringe connection of the enclosed filter. Thereby, the filter connection, upon the penetration of the package by a matching connection, e.g., by the conical part of the syringe, is made quickly and positively. When the filter is withdrawn, the segments unfold upwardly out of the way.

In another preferred embodiment of the invention, the pre-formed break lines are designed as tapered areas of the package cover. Such tapered areas have a lesser resistance to breaking than does the remaining area. If a pressure is exerted against the cover surface, then the cover will tend to break precisely along the break lines forming the tapered areas.

In yet another advantageous embodiment of the invention, the pre-formed break lines are made of a different material that has a lesser breaking resistance than the surrounding package cover. Because the break lines are made of a material of less tear resistance than the surrounding package cover, the break lines have an even lesser tear resistance than that which can be achieved by the tapering of certain areas of the cover.

In another embodiment of the invention, the penetration point is designed as a penetrable surface in the center of a tapered area of the filter package cover. It is also possible for this penetrable surface to be composed of a different material than the immediately surrounding filter package cover and to be of lesser tear resistance. A penetrable surface of flat design, which has a lesser tear resistance, eases the penetration of the cover by a syringe cone and leads to a directly aimed joining of the syringe connection on the filter with the syringe cone.

In yet another embodiment of the invention, the package cover is comprised of bound layers, having at least one first continuous layer and at least one second interrupted layer, the latter bound to the former in such a manner that the interruptions form the break lines. In the case of a two-layered cover, a simple and economical cover with break lines can be simply and economically manufactured. The continuous layer exhibits a lesser resistance to tear than does the interrupted layer, so that the package can easily be broken along the break lines formed by the interrupted layer. For this type of construction, the two layers can be made of different materials, so that both the mutual binding and the integration of a different material for the break lines act within a single cover sheet. Both layers can also be of the same material, so that the combined bound layer acts in the same manner as tapered segments of a single cover layer. The layers may also be of different thicknesses, in order to provide a definite resistance to tear.

In a further preferred embodiment of the invention, the penetration point is provided with a special marking of the penetration point, for instance, in the form of a color marking.

Conventional filter packages have a small distance between the package cover and the syringe connection. When the cover is penetrated, under certain conditions, the flaps of the cover at the penetration point move into the syringe connection and jam themselves between the syringe's cone and the inner wall of the syringe connection. Also, under certain circumstances, remnants of the package are pushed into the filter holder and the function of the filter membrane is impaired.

In a further preferred embodiment of the invention, there exists between the package cover and the syringe connection a sufficient distance, that during the penetration of the package cover through the penetration point, inwardly folding segments of the package cover do not touch the syringe connection. Furthermore, the impingement of package remnants with the syringe connection is prevented by setting a sufficient distance between the cover and the syringe connection which also lessens the danger that parts of the remnants become freed, allowing them to reach the filter membrane.

In a further advantageous embodiment of the invention, the package housing, in a section proximal to the needle connection, is designed so as to permit the withdrawal of the disposable filter by exerting pressure from the outside and bottom of the housing. In this embodiment the distance between the syringe connection and the package cover can be minimized. To this end, the housing section in the area of the needle connection can be designed to be somewhat pliable and can be given a contour which conforms to the needle connection. For instance, the package housing or at least a portion thereof, can be made of an easily deformable material such as a pliable plastic.

In a final preferred embodiment of the invention, the package housing is sealed against contamination with a circumferential flange in the area of the filter membrane. For applications with especially severe demands on sterility, such a contamination-tight closure of the outer rim of the filter holder with the package housing offers an additional protection of the downstream zone in the area of the needle connection. This is so, because even after the opening of the package cover, the downstream zone nevertheless remains closed, and is freed only by the actual withdrawal of the filter.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A filter package comprising a housing and a cover and adapted for containing a sterile disposable filter comprising a filter membrane in a filter holder, said filter holder having a syringe connection proximal to said cover and a needle connection distal to said cover, wherein said cover is provided with a penetrable point that is axially aligned with said syringe connection and with at least one pre-formed break line, along which said cover, upon application of force, tears open so as to permit said sterile disposable filter to be withdrawn.

2. The filter package of claim 1 wherein said cover is provided with two intersecting break lines, the intersection of which forms said penetrable point.

3. The filter package of claim 2 wherein said intersecting break lines divide said cover into four segments.

4. The filter package of claim 2 wherein said break lines form tapered areas of said cover.

5. The filter package of claim 2 wherein said break lines consist of a different material of less tear resistance than the material of the immediately surrounding cover.

6. The filter package of the claim 2 wherein said penetrable point is made from a different material of lesser tear resistance than the material of the immediately surrounding cover.

7. The filter package of claim 2 wherein said cover is formed of bonded layers comprising (i) at least one continuous layer and (ii) at least one discontinuous layer having discontinuities bonded to said continuous layer so that said discontinuities form said break lines.

8. The filter package of claim 7 wherein said bonded layers are of different materials.

9. The filter package of claim 8 wherein said bonded layers have different thicknesses.

10. The filter package of claim 1 wherein said penetrable point is marked.

11. The filter package of claim 1 wherein said housing is deformable in the area of said needle connection.

12. The filter package of claim 11 wherein said housing has a contour fitting that of said needle connection in the area of said needle connection.

13. The filter package of claim 1 wherein said housing has a circumferential flange disposed around said cover.

* * * * *